US009533091B2

(12) United States Patent
Solomon (10) Patent No.: US 9,533,091 B2
(45) Date of Patent: Jan. 3, 2017

(54) SYSTEM AND METHOD OF EFFICACIOUS BODY CAVITY WASHING

(71) Applicant: Hana R. Solomon, Columbia, MO (US)

(72) Inventor: Hana R. Solomon, Columbia, MO (US)

(73) Assignee: BeWell Health, LLC, Columbia, MO (US)

( * ) Notice: Subject to any disclaimer, the term of this patent is extended or adjusted under 35 U.S.C. 154(b) by 0 days.

(21) Appl. No.: 13/833,355

(22) Filed: Mar. 15, 2013

(65) Prior Publication Data

US 2013/0289495 A1   Oct. 31, 2013

Related U.S. Application Data

(63) Continuation-in-part of application No. 12/316,620, filed on Dec. 15, 2008, now abandoned.

(51) Int. Cl.
*A61M 3/00* (2006.01)
*A61M 3/02* (2006.01)

(52) U.S. Cl.
CPC ............ *A61M 3/02* (2013.01); *A61M 3/0262* (2013.01); *A61M 2205/583* (2013.01); *A61M 2206/10* (2013.01); *A61M 2210/0618* (2013.01)

(58) Field of Classification Search
CPC ................... A61M 2205/583; A61M 2206/10; A61M 2210/0618; A61M 3/02; A61M 3/0262
USPC ..... 604/19, 36, 37, 257, 514, 516, 275, 260; 128/200.21–200.24
See application file for complete search history.

(56) References Cited

U.S. PATENT DOCUMENTS

| | | | |
|---|---|---|---|
| 638,481 A | 12/1899 | Seltzer | |
| 692,485 A | 2/1902 | Seltzer | |
| 716,931 A | 12/1902 | Pattison | |
| 1,126,827 A | 2/1915 | Moellering | |
| 2,292,474 A | 8/1942 | Paxton | |
| 2,514,744 A * | 7/1950 | Cipyak | 215/11.1 |
| 5,116,311 A | 5/1992 | Lofstedt | |
| 5,806,723 A * | 9/1998 | DuBose | 222/211 |
| 5,857,991 A | 1/1999 | Grothoff et al. | |
| RE36,070 E | 2/1999 | Ballini et al. | |
| 5,899,878 A | 5/1999 | Glassman | |
| 6,070,573 A | 6/2000 | Howe et al. | |
| 6,361,521 B1 | 3/2002 | Erickson | |
| 6,446,821 B1 * | 9/2002 | Salisbury | 215/11.1 |
| 6,540,718 B1 * | 4/2003 | Wennek | 604/94.01 |
| 6,604,642 B1 * | 8/2003 | Barruw | 215/40 |
| 6,701,916 B2 | 3/2004 | Mezzoli | |
| 6,802,823 B2 | 10/2004 | Mason | |
| 6,823,862 B2 | 11/2004 | McNaughtan | |
| 6,955,169 B2 | 10/2005 | Khan | |
| 7,862,548 B2 * | 1/2011 | Javer | A61H 35/04 604/212 |

(Continued)

*Primary Examiner* — Imani Hayman
(74) *Attorney, Agent, or Firm* — Lewis Rice LLC (57) ABSTRACT

Systems and methods of efficaciously washing body cavities, specifically including the nasal cavity, wherein a fluid flow is governed in at least one of degree and direction of issuance. Governing of the degree of fluid flow can involve an applicator that is affixable to a fluid source, wherein the applicator can variably constrain the degree of fluid flow being issued. Governing of the direction of issuance can involve the applicator, when affixed to the fluid source, issuing the fluid flow in a specific direction, relative to the fluid source, and an indicator of the fluid source's general orientation relative to vertical.

5 Claims, 7 Drawing Sheets

(56) References Cited

U.S. PATENT DOCUMENTS

2007/0262096 A1\* 11/2007 Gaynes ................ A61M 31/00
 222/420
2008/0029086 A1 2/2008 Harlan et al.
2011/0184341 A1 7/2011 Baker et al.

\* cited by examiner

SYSTEM AND METHOD OF EFFICACIOUS BODY CAVITY WASHING

CROSS REFERENCE TO RELATED APPLICATIONS

This Application is a Continuation-in-Part (CIP) of U.S. patent application Ser. No. 12/316,620, filed Dec. 15, 2008 and currently pending, the entire disclosure of which is incorporated herein by reference.

BACKGROUND

1. Field of the Invention

The present invention relates generally to systems and methods of washing a body cavity, and in particular to systems and methods of affecting a flow of field, including affecting the flow's disposition or degree, to provide efficacious washing of a body cavity.

2. Description of the Related Art

For many health or comfort care situations, utilizing an appropriate manner of applying a treatment can be nearly as critical to the treatment's effectiveness as correctly selecting a treatment that is suitable for the issue being treated. The consequences of misapplication can range from a relatively benign lack of relief, to a more serious initiation of an additional issue due to the misapplication, on up to an abandonment of treatment altogether, or even a switch to a differing, potentially even dangerous alternative treatment when the original treatment is still the best choice if applied properly. In many cases, the potential for misapplication is particularly prevalent when the treatment itself is a deceptively simple, everyday action. Washing of a body cavity is such an easily misunderstood treatment that the present invention provides systems and methods for ensuring its efficacious application.

A variety of body cavities, such as the nasal cavity or the vagina, are potentially benefited by washing with externally applied techniques. A difficulty common among many of these cavities is that while the individual is, of course, quite familiar with the cavity in many senses, it is also generally not possible for the individual to see well within the cavity, nor to be exactly aware of the detailed internal structure and topography of their own cavity, since there are variations from person-to-person. Since many of the treatments available are preferably applied in particular dispositions relative to the cavity, and/or are best conducted in particular manners that are not easily regulated, especially when an individual is self treating, a significant potential for misapplication is common. Among the more frequent situations where body cavity washing can be beneficial, and a useful illustration of the difficulties addressed by the present invention, is the practice of washing (or cleansing) the nasal cavity.

An understanding of the benefits of efficacious nasal washing has a long history in numerous cultures. Nasal washing or nasal irrigation is an ancient Ayurvedic technique known as Jala neti, which literally means "nasal cleansing" in Sanskrit (a classical language of South Asia). With origins based in the yoga tradition, nasal washing has been an accepted practice throughout India and South East Asia. Although not as historically common in Western cultures, these Eastern cultures have performed Jala neti as routinely as brushing one's teeth for centuries. Traditionally, a neti pot (which is a tea pot or Aladdin's lamp shaped vessel) has been used to flow salt water into one nostril, through the sinus cavities and out the other nostril. In the West, for over a century now, doctors have also come to appreciate the benefits of nasal washing. Alfred Laskiewicz, departmental Head of Pozna Otolaryngology Department (1932-1939) at the time, described conservative treatments of nasal irrigation from general hygiene to treatment of Scleroderma. The Proetz procedure has been used by ear, nose and throat surgeons for years to irrigate the sinuses after surgery.

Many forms of equipment have been utilized to effect nasal lavage including gravity flow vessels, pressure bottles, powered machines, misters, IV bags, sprays, squirts, flushers, bulbs, syringes, squeeze bottles, and even turkey basters. In addition to diversely configured physical modes of executing nasal washing, an assortment of differing types of wash solutions have also been employed. Most often, these solutions primarily consist of various salt solutions. Among those that have been studied are salt rinse formulations that are isotonic, hypertonic, or buffered, as well as those with additives such as colloidal silver, antibiotics and herbs. (An isotonic solution has the same salt concentration as the human body, a hypertonic solution bas a greater salt concentration than the human body, and a buffered solution, in this context, is less acidic and is often generally better tolerated as well as potentially more effective.) The overall effectiveness of nasal washing has been repeatedly supported by the results of these scientific investigations. Currently, a hypertonic buffered saline solution has been shown to be most effective in treatment of congestion, along with removal of infectious and allergenic particles, but an isotonic buffered saline solution works well for overall daily washing.

Over the past decade, a slowly growing expansion of interest in nasal cleansing has taken root in the United States. Among the factors contributing to this growth are the overall surge in appeal of preventative and alternative medicine, as well as a mounting trend towards an integrative approach to healthcare. Although antihistamines, decongestants, steroids, mucolytics, immune modulators, and antibiotics are already commonly prescribed for various nasal and sinus health issues, doctors have increasingly also added the adjunct treatment of nasal irrigation for allergy suffers, post operative sinus surgery patients, and for patients with chronic sinusitis. Recently, proactive nasal washing is being recommended as a preventative approach for these health conditions. The benefits of nasal washing include refreshing, cleansing and moisturizing the nasal membranes. A lack of washing can produce substantial discomfort and health complications (such as allergic reactions, nasal congestion, sinus infections, post nasal drip, sore throat, asthma or nasal discharge) when not in optimal condition, as most people can personally attest. When washing with a hypertonic salt mixture, the nasal and sinus environment become more difficult for bacterial or viral growth.

Presently, many products are available to enable implementing nasal, washing more quickly, more easily, more effectively, and with less resulting mess. Even with such an extensive history of addressing the issue of nasal cleansing, substantial problems in ensuring that nasal cleansing is reliably efficacious remain unsolved, however. Among the principal problems remaining are that the vast majority of approaches do not account for the particulars of the physical arrangement of the nasal cavity, which impacts both the preferable manner and degree of nasal washing action. Most prior systems and methods enable introducing the wash solution to the nasal cavity without also enabling improved control and guidance of the manner of introduction (for example, washing pointing upwards can be uncomfortable), much less discernment, during the washing process itself, as to any aspect of whether the solution is being appropriately applied. In sum, it is difficult, if not impossible, for users of the current systems to ascertain the correct angle at which they must hold the nasal washing apparatus and their upper body when applying the cleansing solution to the nasal cavity. This is problematic because, among other things, improper application of nasal solution in the nasal cavity can result in an uncomfortable feeling for a user (e.g., the user feels like they are drowning) and improper cleansing of the nasal cavity. Further, improper insertion of a nasal washing apparatus and application of nasal washing solution has the potential to introduce contaminants, pollutants, infectious particles and debris into the sinus cavity. The frustration associated with this discomfort and confusion regarding application can lead user's to abandon the nasal washing process altogether, thereby forgoing a maintenance ritual with could positively impact their health.

Accordingly, there is a need in the art for a nasal washing apparatus and system whose application is easily understood and carried out by the user, in addition to nasal washing apparatuses that provide additional features to increase the comfort of nasal washing.

SUMMARY

At the core of much of the present invention's benefits is the recognition that the internal geography of the nasal cavity (as well as other body cavities) is not arranged to readily facilitate the washing of the cavity in general, much less specific washing objectives, from outside of the cavity. While it is possible to access the interiors of these cavities, one will still be essentially "driving in the dark" without a surgical or other procedure to provide inspection (obviously a problematic approach for an everyday action). The exact particulars of the cavity's internal topography need to be properly addressed to achieve the desired results, and an understanding of both these challenges and the advantages provided by the present invention can be well illustrated by once again specifically considering the nasal cavity. In order to accomplish its various functions, the nasal cavity has evolved to pack a substantial amount of surface area into a relatively limited amount of volume. Not only is the nasal cavity interior volume demarcated by a complex manifold, but the conduits between the nasal cavity and the other spaces it interconnects with (e.g., sinuses and the inner ear) may provide only diminutive ostia for fluids to communicate between. An important objective of nasal washing is to improve drainage from these spaces, through the nasal cavity, and provide relief from excess pressure.

The present invention facilitates and enhances the intercommunication of fluids and pressures between the nasal cavity and the other spaces by providing modes of administering a flow of fluids that influence the ostia to open. Even if practical, directly applying a washing fluid flow to the ostia, via the nasal cavity, is generally not advantageous. The ostia's minute dimensions, along with their and the nasal cavity's tendency to already contain blocking, or potentially blocking debris, produces a likelihood that they become even more obstructed because the directly applied fluid flow can pack the debris into the ostia. Furthermore, the desired normal mucous flow direction is out through the ostia into the nasal cavity, not back into the sinuses or inner ear, as would occur when a fluid flow is directly applied to the ostia from within the nasal cavity. Among the key achievements of the present invention is its ability to govern the conduct of a fluid flow administered to the nasal cavity, through queues to a user regarding proper application of the solution to the nasal cavity and regulation of the flow from the nasal washing apparatus into a user's nasal cavity, so that the ostia are influenced to open and provide intercommunication between the nasal cavity and the other intra-head spaces.

The present invention, by governing a fluid flow's specific conduct into and at least partially through the nasal cavity, utilizes Bernoulli's principle to enact its impact on the ostia. Bernoulli's principle, roughly synopsized, states that as a fluid flow's speed increases its surface pressure decreases. Hence, when a flow of fluid is conducted into and at least partially through the nasal cavity with a suitable trajectory and velocity so that the ostia encounter the reduced surface pressure due to Bernoulli's principle, passage of fluid and other matter within the intra-head passages that interconnect with the nasal cavity will be influenced to drain into the nasal cavity via the ostia. It can be decisive that appropriate conduct of the fluid flow be readily achieved by the user, or the desired effect upon the ostia will not be reliably realized. The appropriate conduct involves directing the flow of fluid across the floor of the nasal cavity so it can flow past the sinus and other ostia, creating pressure differentials that encourages the draining of the sinus' contents. Incorrectly directing the fluid flow upward, rather than backward, may aim it directly at the openings to the sinuses, potentially not only blocking outward flow through the ostia, but possibly also causing transient discomfort as pressure is forced into inadequate spaces. The avoidance of this prospect of discomfort is another primary benefit of the present invention.

A significant attribute of embodiments of the present invention are their provision of at least one flow influencing feature that produces effects upon a fluid flow administered to the user to achieve the benefits described. Various embodiments of the present invention govern the conduct of the fluid flow by, among other manners, indicating the orientation of the fluid flow relative to vertical with a first flow influencing feature and by providing a variable restrictability of the degree of the fluid flow with a second flow influencing feature. By receiving an indication of the fluid flow's orientation relative to vertical, the user is able to properly direct the flow in the manner required while still being able to hold their head and neck in a natural upright and neutral position, thereby ensuring both that the user is comfortable (to promote regular use) and that the user is able to readily replicate the proper positioning of the flow relative to their head by allowing them to administer the flow with their head held in an repeatedly attainable, easily maintained neutral position.

Among other ways, the present invention provides manners of suitably directing the fluid flow, relative to vertical, by providing the user an indication of the orientation, relative to vertical, of a source of the fluid flow being administered. The source is interrelated with an applicator that governs the issuing fluid flow by at least one of influencing the direction of the issued fluid flow and variably restricting the fluid flow's degree. In regard to influencing the direction of the fluid flow, some embodiments of the applicator can govern the fluid flow to issue in a known, or even specified, direction relative to the source; which, in combination with the indication of the source's orientation relative to vertical, allows the user to attain and maintain the fluid flow in a given orientation relative to vertical. Hence, by holding the head neutral, arranging the fluid flow in a selected orientation (generally perpendicular) relative to vertical, and suitably placing the applicator and source at the nasal cavity opening the user can reliably and easily direct the fluid flow correctly for efficacious nasal washing.

Various embodiments of the present invention include, sometimes as an optional feature, a second flow influencing feature for governing the conduct of the fluid flow: an applicator able to variably restrict the cross-section of a passage that the fluid flow traverses in order to impact its degree of flow. Some embodiments of the present invention, such as those that include a resiliently deformable reservoir, are capable of providing a fluid flow that can be highly changeable in degree. While this changeability can provide a capability that is advantageous to some, who appreciate the option to flexibly choose bow great a degree of flow they will to attempt to apply, others will prefer an ability to ensure that the flow is at least somewhat constrained so that it is, for example, more predictable in degree or requiring less concentration or less user ability to exert physical control of the reservoir deformation. In certain circumstances, the fluid flow degree's restrictability can be critical for a given user to be able to benefit from a nasal washing treatment, such as when a medical condition can present negative complications if the body cavity washing is too vigorous, e.g. following nasal surgery. A major factor in the long-term success of body cavity washing can be conditional upon the user utilizing the washing treatment on a consistent basis, so that any manner of washing that presents a significantly improved comfort level can, by promoting such consistent use, result in a substantially more efficacious treatment. The present invention can accomplish such a substantially improved treatment result by its provision of features that can also greatly improve the comfort level of the user.

Other objects and features will be in part apparent and in part pointed out hereinafter.

DETAILED DESCRIPTION OF THE PREFERRED EMBODIMENTS

In the following description, identical numbers indicate identical elements. Where an element has been described in one Figure, and is unaltered in detail or relation in any other Figure, said element description applies to all Figures.

Figure 1:
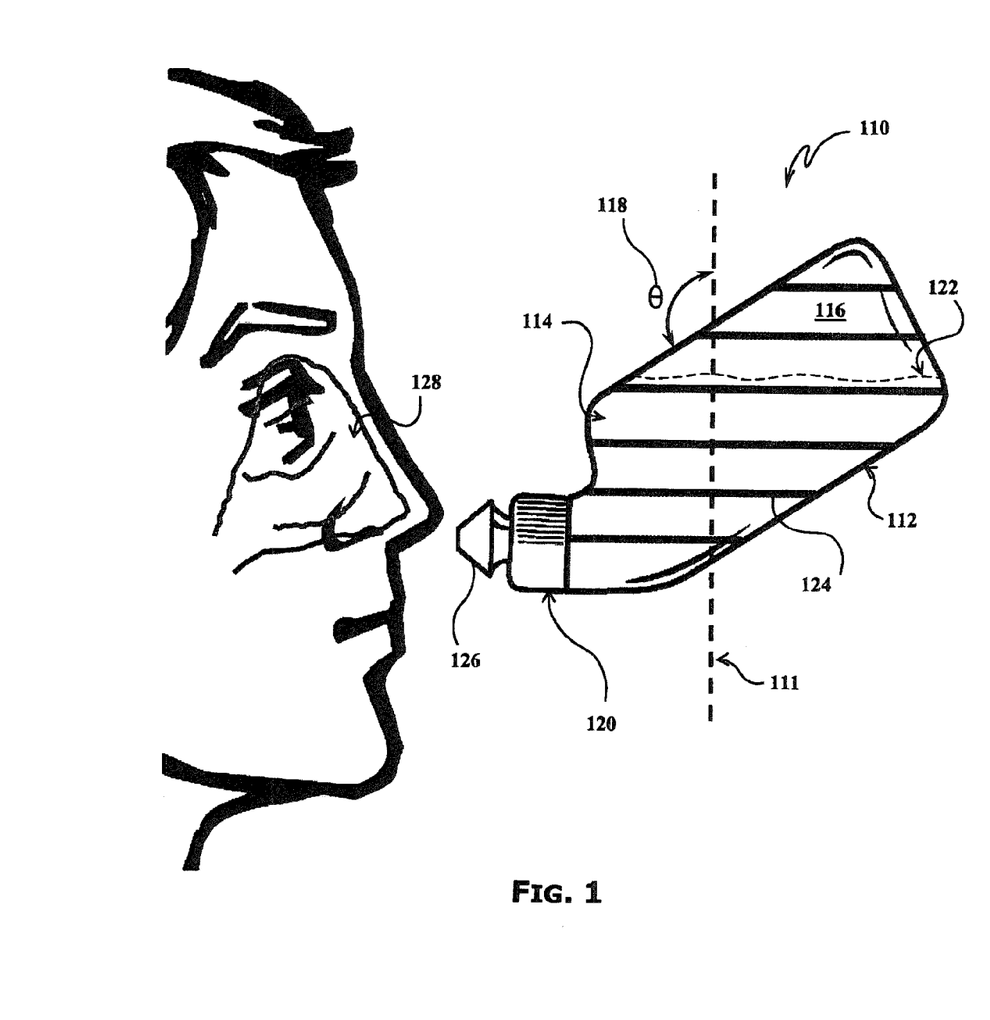
FIG. 1 depicts a schematic cross-section view of an orientation indicating embodiment of the present invention disposed relative to a user in a specific orientation relative to vertical and includes a schematic cross-section view of the user's nasal cavity.

A first orientation indicating embodiment (110) of the present invention, shown in FIG. 1, is depicted in a representative usage situation, about to be repositioned towards the nostril of the individual user depicted. The reference attribute, relative to vertical (indicated by the dashed line (111)), for the first orientation indicating embodiment (110) is predicated to be the longitudinal wall (112) of the fluid source's main body (114). In certain embodiments the fluid source's main body (114) is also a reservoir for those embodiments. For the first orientation indicating embodiment (110) depicted in FIG. 1, the main body (114) is also serving to provide a reservoir (116). The longitudinal walls (112) which may comprise one or more interconnected sections define the longest dimension of the main body (114) and hence are a straightforward selection as defining the orientation of the first orientation indicating embodiment (110). Hence, when the longitudinal wall (112) is shown as disposed at an angle θ (118), relative to vertical, the first orientation indicating embodiment (110) will then be described as being oriented at an angle θ (118), relative to vertical, as well. A fluid level in the reservoir (116) is indicated by the surface (122) of the fluid contained within the reservoir (116). At least some portions of the longitudinal walls (112) are constructed to be at least partially transparent so that the user can see the fluid surface (122). Since the fluid steam (122), in response to gravity, will assume a general disposition perpendicular to vertical (111), comparison of the orientation of the first orientation indicating embodiment (110) to the orientation of the fluid surface (122) will reveal the orientation of the first orientation indicating embodiment (110) relative to vertical (111). For appropriate use of the first orientation indicating embodiment (110), it is not necessary to ascertain its orientation in general, but merely to ascertain if it is in the desired orientation, relative to vertical (111), in order to properly direct the fluid flow. At least one, and usually a plurality of, aligned indicia (124) are arranged on at least a portion of the periphery of the main body (114), particularly including at least some of the at least partially transparent portions of the longitudinal walls (112). By visually aligning, at least roughly, at least one indicia with the fluid surface level (122), the user can align and maintain the first orientation indicating embodiment (110) in a desired orientation relative to vertical. Disposed in such a desired orientation relative to vertical, the first orientation indicating embodiment (110) is located with the applicator (126) in contact with the nostril so that the fluid flow can be administered in the desired direction to a nasal cavity (128).

Figure 5:
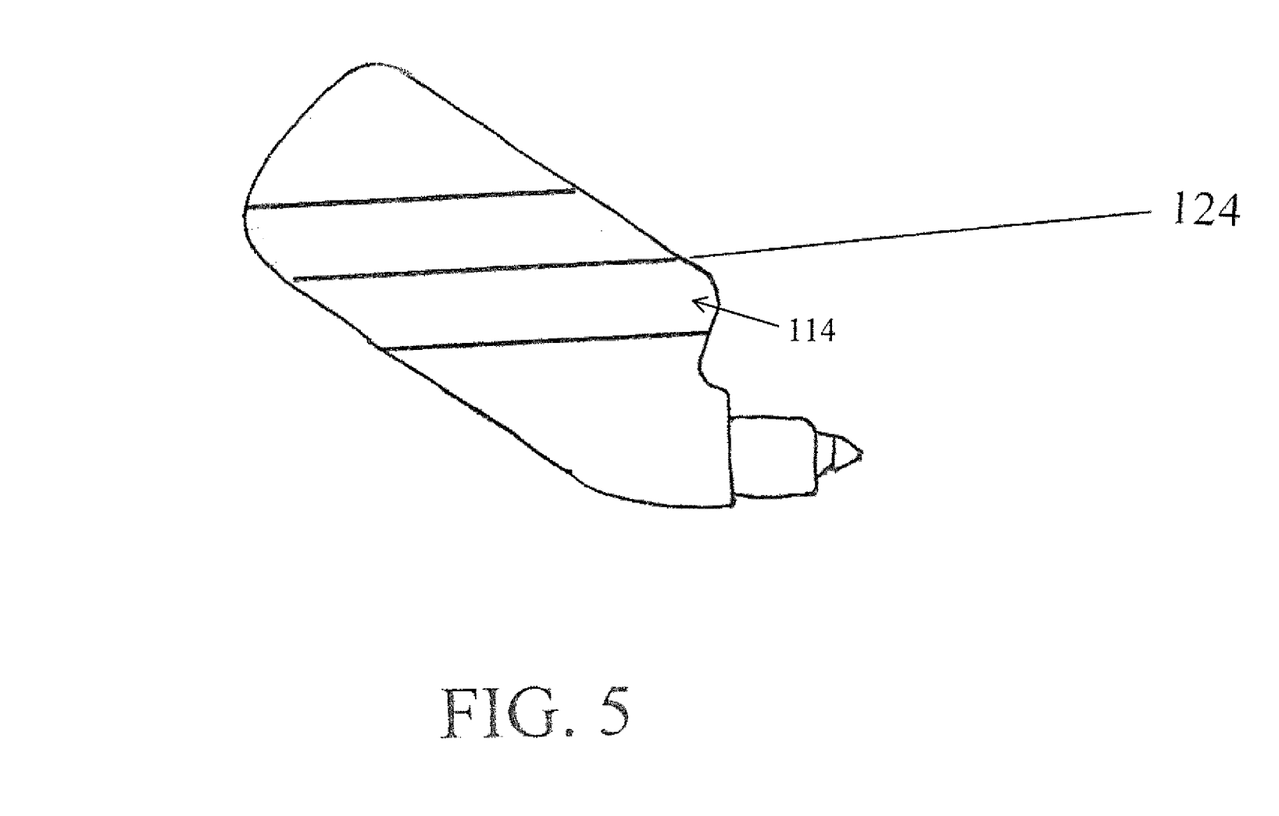
FIG. 5 depicts an embodiment of the nasal washing apparatus with one or more aligned indicia.
Figure 6:
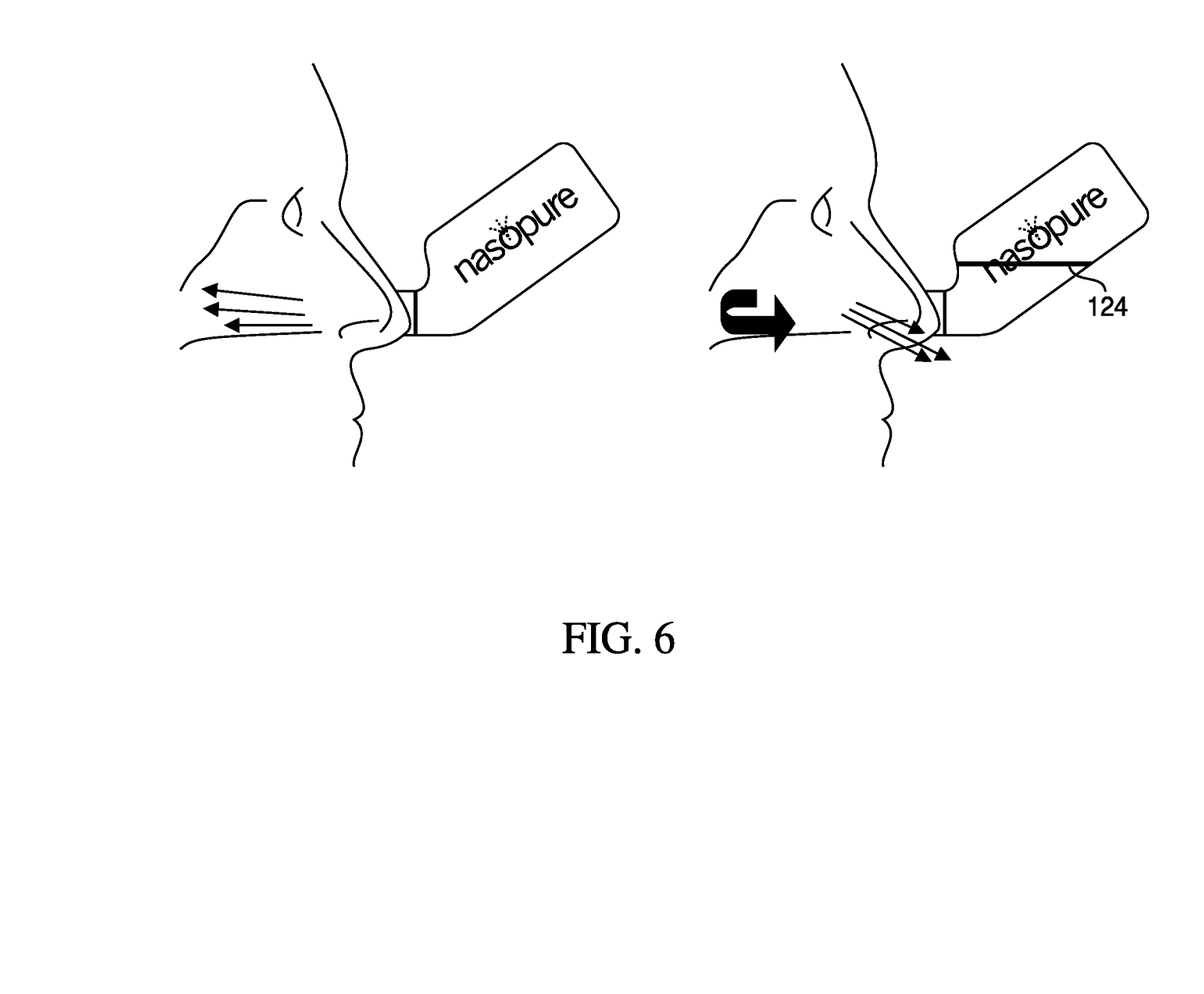
FIG. 6 depicts an embodiment of the nasal washing apparatus with one or more aligned indicia in which the nasal washing apparatus is aligned with one of the one or more aligned indicia during application.
Figure 7:
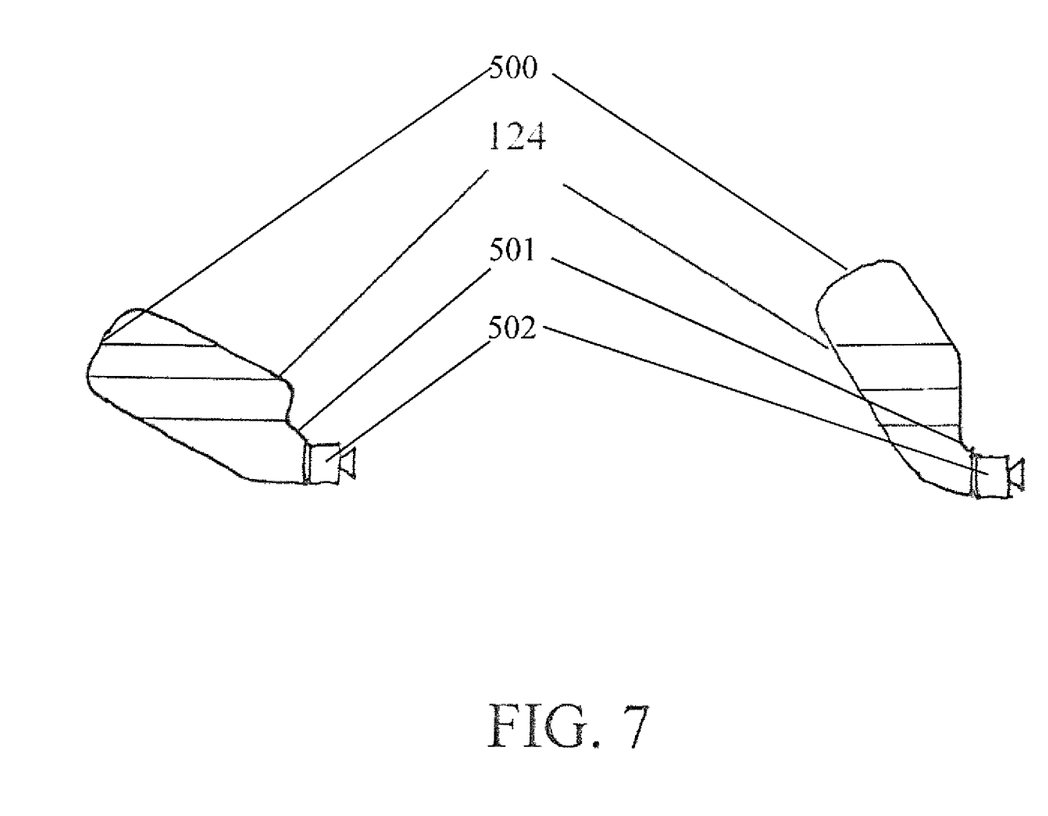
FIG. 7 depicts an embodiment of the nasal washing apparatus with an angled neck at variable degrees.

Accordingly, in one embodiment, described herein is a nasal washing apparatus, as demonstrated in FIGS. 5-6, with one or more aligned indicia (124), the one or more aligned indicia (124) notifying the user of the proper location for the fluid surface level (122) of the nasal solution housed in the main body (114) of the nasal washing apparatus during application when a user's head is located in a neutral position. These one or more aligned indicia (124) offer the user an easy-to-decipher and apply guide for the orientation of the nasal washing apparatus during application so as to ensure proper application of the nasal washing solution in a person's nasal cavity. Further, in another embodiment, described herein, as depicted in FIG. 7, is a nasal washing apparatus comprised of a bottle (500), an angled neck (501), a dispensing means (502) and one or more aligned indicia (124) designating the internal solution level, and thereby the proper application of the nasal solution, wherein the angle of the neck (501) is between 45 degrees and 89 degrees and 1 degree and 44 degrees. Contemplated dispensing means for this embodiment include any dispensing means know to those of ordinary skill in the art for applying a solution to a nasal cavity including, but are not limited to, the variably restricted applicator (310) disclosed herein.

Figure 2:
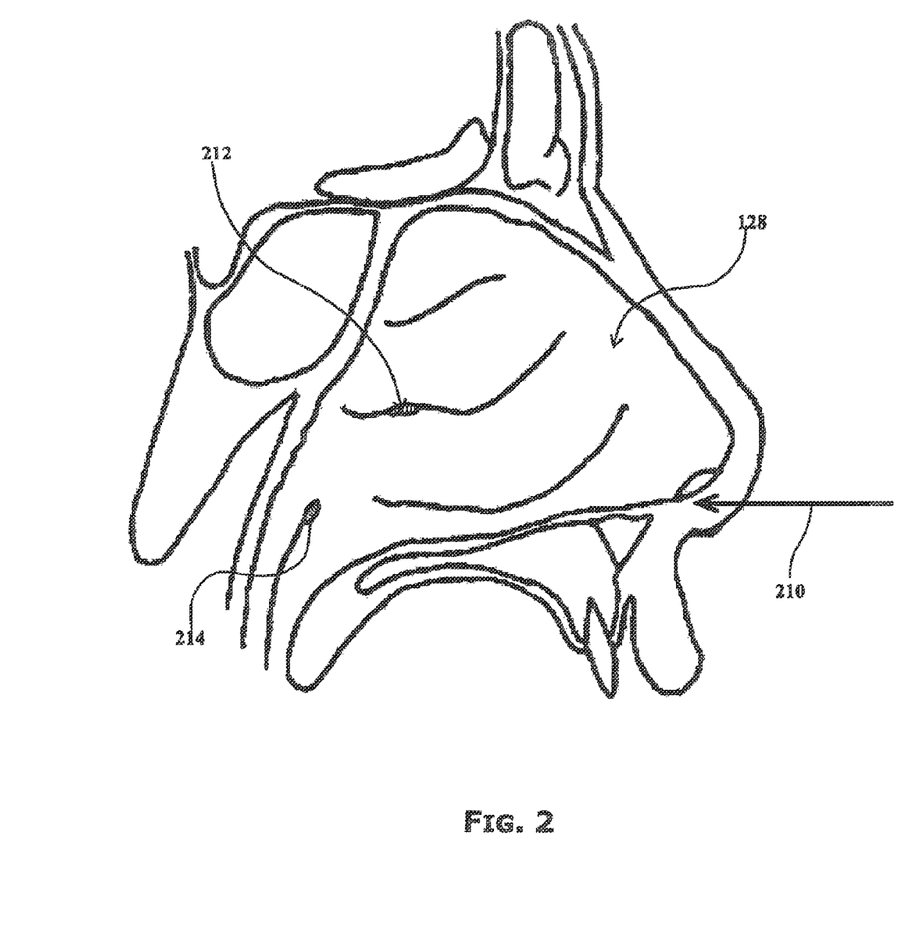
FIG. 2 depicts an expanded schematic cross-section view of a user's nasal cavity with relevant anatomical aspects detailed.

The nasal cavity (128) is depicted in substantially greater detail in the cross-section shown in FIG. 2. The desired direction (210) and disposition of fluid flow administration is shown as entering along the floor of the nasal cavity (128), where it will interact with the complicated internal space within the nasal cavity (128). The majority of the details of this complicated internal space will not be explicated in depth herein, since it is well known to those of skill in the art and the details are easily available by consultation of an innumerable assortment of references. However, two specific aspects of this internal space will be described in detail since they are particularly germane to the benefits provided by the present invention. As described earlier, the ostia within the nasal cavity (128) are diminutive orifices that enable intercommunication between the nasal cavity (128) and other spaces within the head, and their specific locations impact the difficulties encountered in clearing these other spaces via the nasal cavity (128) and in being able to promote their opening when blocked. A sinus ostia (212) and the ostia interconnecting the inner ear (214) are shown in their general dispositions in the schematic drawing depicted in FIG. 2, although it should be understood that these locations can and often will vary, at least somewhat, from individual-to-individual, with their basic dispositions usually corresponding at least approximately with the FIG. 2 depiction. It is clear that direct access to these ostia is not readily available even to a trained medical professional, much less to an, everyday, self-treating layman.

Figure 3:
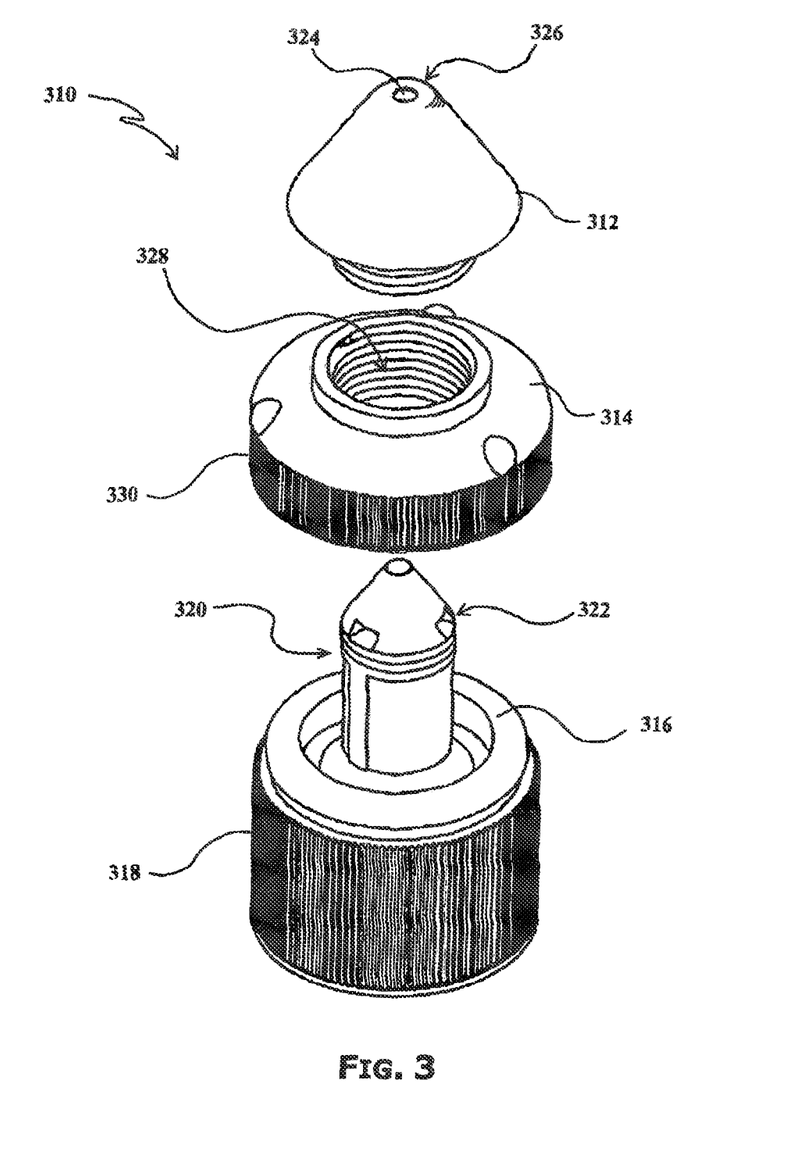
FIG. 3 depicts a schematic exploded view of components of an embodiment of an applicator according to the present invention.

As discussed earlier, an efficaciously conducted fluid flow according to the present invention can include a manner of governing the degree of fluid flow, such as by utilization of the first variably restrictable applicator (310), depicted in an exploded view in FIG. 3, the first variably restrictable applicator (310) comprises three primary sub-parts, an applicator tip (312), and intermediate variable restrictor (314), and an applicator base (316). The applicator base (316) interconnects with a throat portion (318) to the main body (114), and includes an internal passage (not shown) that, when interconnected with the main body (114), allows fluid within the reservoir (116) to access a conduit (320) which terminates in at least one port (322). When the first variably restrictable applicator (310) is assembled, as shown in cross-section in FIG. 4, the at least one port (322) opens into an interior volume (not shown) of the applicator tip (312). The interior volume of the applicator tip (312) interconnects with an aperture (324) through which the fluid flow can emerge. An exterior terminus (326) of the applicator tip (312) is shaped to allow a close fit with the nasal cavity orifice, without allowing substantial, potentially damaging entry to the nasal cavity (128). The intermediate variable restrictor (314) both fits around and upon the applicator base (316), often though not exclusively with a snap and ridge interconnection, and provides an, interior channel (328) through which the conduit (320) is inserted until the at least one port (322) enters the interior volume of the applicator tip (312). The applicator tip (312) is interconnected with the intermediate variable restrictor (314), often though not exclusively with a screw-thread interconnection, so that rotational movement of the intermediate variable restrictor (314), for example enacted by gripping and torquing the ridges (330), will move the applicator tip (312). When the intermediate variable restrictor (314) is turned relative to the applicator base (316), the applicator tip (312) is movable both closer and farther, depending on the direction of turning, form the applicator base (316), which in turn provides progressively lesser or greater, respectively, space between the at least one port (322) and the interior surface of the applicator tip (312). When more space is provided, a greater degree of fluid flow is permitted, and when lesser space is provided, fluid flow is thereby restricted to being only a lesser degree.

Figure 4:
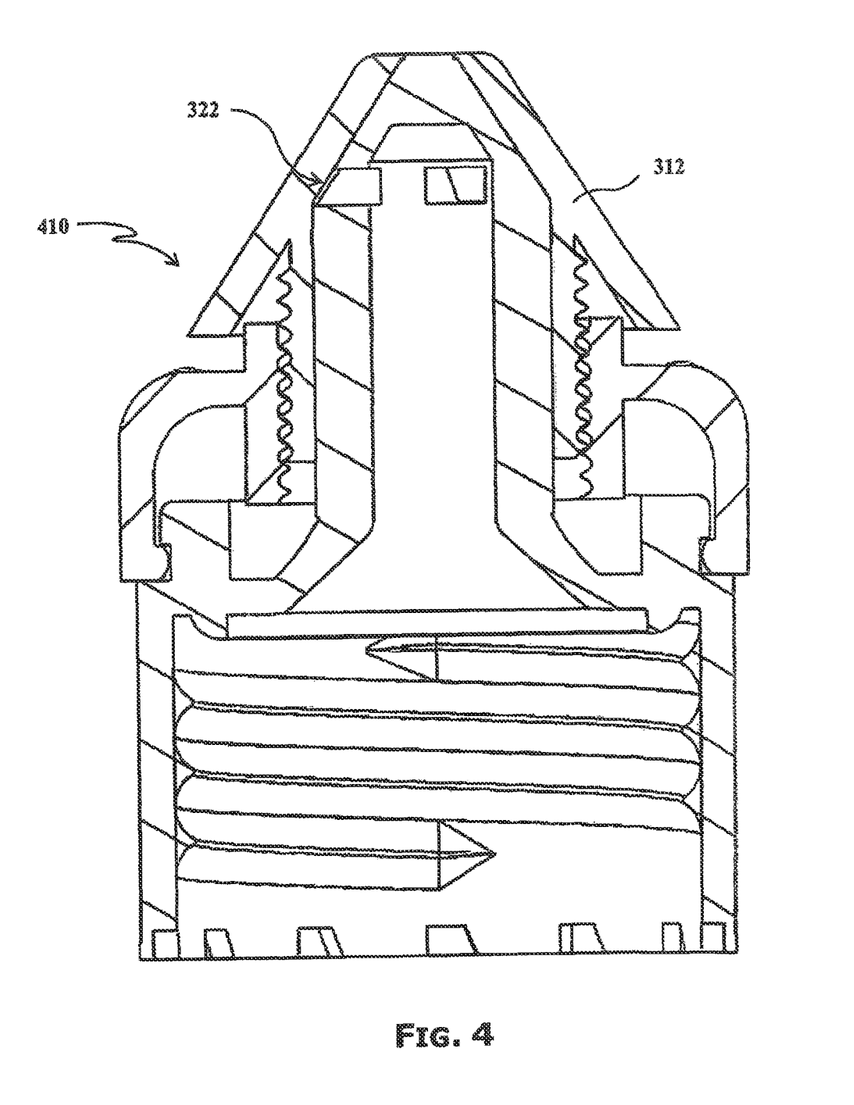
FIG. 4 depicts a schematic cross-section view of an assembled embodiment of an applicator according to the present invention.

An assembled applicator cross-section view (410) of the first variably restrictable applicator (310) in FIG. 4 depicts the applicator tip (312) in a maximally fluid flow restricting disposition. In this maximally fluid flow restricting disposition, it can be seen that the at least one port (322) is almost flush with the interior surface of the applicator tip (312), and hence only a minimal amount of fluid flow is able to pass through the at least one port (322). Although not shown, it is readily understandable that by moving the applicator tip (312) further away from the at least one port (322), as described immediately above, progressively greater amounts of fluid flow are able to pass.

In view of the above, it will be seen that the various objects and features of the invention are achieved and other advantageous results obtained. The examples contained herein are merely illustrative and are not intended in a limiting sense.

The invention claimed is:

1. A nasal washing apparatus for efficacious washing of a nasal cavity, the apparatus comprising:
   a main body comprising a longitudinal wall and forming a reservoir for a solution;
   one or more aligned indicia located on the longitudinal wall; and
   a dispenser configured to apply a stream of said solution to the nasal cavity;
   wherein the one or more aligned indicia are arranged at a non-perpendicular angle relative to the longitudinal wall and are configured to offer a user a guide for the orientation of the nasal washing apparatus during washing of the nasal cavity by the user aligning a level of the solution in the reservoir to be generally parallel to the indicia on the longitudinal wall when the longitudinal wall is at an angle from the vertical.

2. A method of efficacious washing for a user's nasal cavity, the method comprising:
   providing a nasal washing apparatus, the nasal washing apparatus comprising:
      a main body comprising a longitudinal wall and forming a reservoir with a solution therein;
      a plurality of aligned indicia located on the longitudinal wall at a non-perpendicular angle thereto; and
      a dispenser;
   inserting the dispenser into a user's nostril;
   orienting the longitudinal wall at an angle from the vertical until the solution is generally parallel to one of the plurality of aligned indicia;
   and dispensing the solution through the nostril and into the nasal cavity after the solution is aligned.

3. A nasal washing apparatus for efficacious washing of a nasal cavity, the apparatus comprising:
   a main body comprising a bottle and a neck;
   one or more aligned indicia located on the bottle at a non-perpendicular angle thereto; and
   an applicator tip configured to apply a stream of solution in the bottle to the nasal cavity, the applicator tip attached to the neck;
   wherein the neck is arranged at an angle to the bottle; and
   wherein the one or more indicia are arranged at the same angle relative to the bottle as the neck.

4. The nasal washing apparatus of claim 3 wherein the angle of the neck relative to the bottle is between 45 and 89 degrees.

5. The nasal washing apparatus of claim 3 wherein the angle of the neck relative to the bottle is between 1 and 44 degrees.

\* \* \* \* \*